(12) United States Patent
Zablocki et al.

(10) Patent No.: US 7,022,710 B2
(45) Date of Patent: Apr. 4, 2006

(54) A1 ADENOSINE RECEPTOR ANTAGONISTS

(75) Inventors: Jeff Zablocki, Mountain View, CA (US); Rao Kalla, Cupertino, CA (US); Dewan Zeng, San Mateo, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 73 days.

(21) Appl. No.: 10/897,047

(22) Filed: Jul. 22, 2004

(65) Prior Publication Data
US 2005/0059683 A1    Mar. 17, 2005

Related U.S. Application Data

(60) Provisional application No. 60/489,469, filed on Jul. 22, 2003.

(51) Int. Cl.
*A61K 31/52* (2006.01)
(52) U.S. Cl. .................................. 514/263.2
(58) Field of Classification Search .............. 514/263.2
See application file for complete search history.

(56) References Cited

U.S. PATENT DOCUMENTS

| 6,770,651 | B1 * | 8/2004 | Palle et al. | ............ 514/263.37 |
|---|---|---|---|---|
| 2003/0050272 | A1 | 3/2003 | Palle et al. | |
| 2004/0209899 | A1 | 10/2004 | Palle et al. | |

FOREIGN PATENT DOCUMENTS

| WO | WO 00/73307 A3 | 12/2000 |
|---|---|---|
| WO | WO 01/16134 A1 | 3/2001 |

\* cited by examiner

*Primary Examiner*—Raymond J. Henley, III
(74) *Attorney, Agent, or Firm*—J. Elin Hartrum

(57) ABSTRACT

Disclosed are novel methods of antagonizing the $A_1$ adenosine receptor in a mammal, comprising administering to a mammal in need thereof a therapeutically effective dose of a compound of the formula:

Formula I

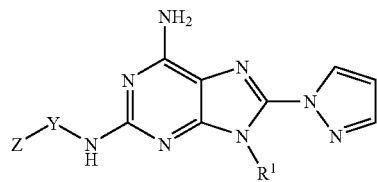

wherein $R^1$ is optionally substituted $C_{1-14}$ alkyl; Y is $C_{1-14}$ alkylene; and Z is phenyl that is optionally substituted with halo, hydroxy, amino, cyano, or optionally substituted $C_{1-4}$ alkyl or a pharmaceutically acceptable salt, ester, or prodrug thereof. The $A_1$ adenosine receptors are antagonized in order to treat a disease state is chosen from renal failure, renal dysfunction, nephritis, hypertension, edema, Alzheimers disease, stress, depression, cardiac arrhythmia, restoration of cardiac function, congestive heart failure, diabetes, asthma, respiratory disorders, ischemia-induced injury of the brain, heart and kidney, and diarrhea.

9 Claims, No Drawings

A1 ADENOSINE RECEPTOR ANTAGONISTS

CROSS REFERENCE TO RELATED APPLICATIONS

This application claims priority to U.S. Provisional Patent Application Ser. No. 60/489,469, filed Jul. 22, 2003, the complete disclosure of which is hereby incorporated by reference.

FIELD OF THE INVENTION

The present invention relates to compounds that are $A_1$ adenosine receptor antagonists, and to their use in treating mammals for various disease states, such as asthma, diabetes, cardiac disorders, degenerative disorders of the central nervous system, and disease states for which diuretic treatment is appropriate.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_1$ adenosine receptor agonists modulate the cardiostimulatory effects of catecholamine, thus slowing the heart rate, and also prolong impulse propagation through the AV node. Thus, stimulation of $A_1$ receptors provides a method of treating supraventricular tachycardias, including termination of nodal re-entrant tachycardias, and control of ventricular rate during atrial fibrillation and flutter. $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

$A_1$ adenosine receptor antagonists have pronounced effects on the kidney, and have shown to be potent diuretics and natriuretics with little effective on potassium excretion. Thus, they are renal protective, useful for the treatment of renal failure, renal dysfunction, nephritis, hypertension, and edema. $A_1$ adenosine receptor antagonists are also useful for treating dementias such as Alzheimers disease, and for treating stress, depression, cardiac arrhythmia, restoration of cardiac function, congestive heart failure, asthma, and respiratory disorders. They also reduce ischemia-induced injury of the brain, heart and kidney, and diarrhea.

It is desired to provide compounds that are potent $A_1$ adenosine receptor antagonists, useful in the treatment of various disease states related to modulation of the $A_1$ adenosine receptor, in particular useful as diuretics.

In U.S. patent application Ser. No. 10/184,494, filed Jun. 27, 2002, novel $A_{2B}$ adenosine receptor antagonists were disclosed. It has now surprisingly been found that a subgroup of the compounds disclosed in this application also have the property of being $A_1$ receptor adenosine receptor antagonists and, in fact, are actually more active as $A_1$ receptor antagonists. Thus, the compounds of Formula I are both $A_{2B}$-antagonists and $A_1$-antagonists, and consequently are effective in the treatment of conditions that respond to administration of $A_{2B}$ adenosine receptor antagonists as well as those conditions listed above for $A_1$ antagonists. Conditions that respond to administration of $A_{2B}$ adenosine receptor antagonists include diarrhea, atherosclerosis, restenosis, diabetic retinopathy, cancer, senile dementia, Alzheimer's disease, Parkinson's disease, traumatic brain injury, and Type I hypersensitivity reactions, including asthma, atopic eczema, and hay fever.

SUMMARY OF THE INVENTION

It is an object of this invention to provide $A_1$ receptor antagonists. Accordingly, in a first aspect, the invention relates to compounds of Formula I:

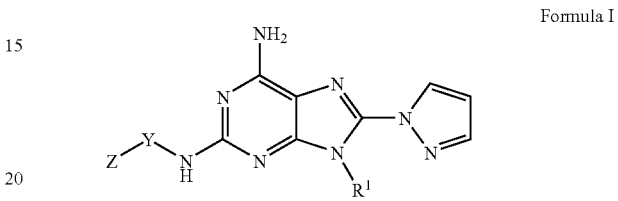

Formula I wherein:
  $R^1$ is optionally substituted $C_{1-4}$ alkyl;
  Y is $C_{1-4}$ alkylene; and
  Z is phenyl that is optionally substituted with halo, hydroxy, amino, cyano, or optionally substituted $C_{1-4}$ alkyl.

A second aspect of this invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be effectively treated with an $A_1$ adenosine receptor antagonist, comprising administering to a mammal in need thereof a therapeutically effective dose of a compound of Formula I. Such diseases include, but are not limited to, disease states for which diuretic treatment is appropriate, renal failure, renal dysfunction, nephritis, hypertension, edema, Alzheimers disease, stress, depression, cardiac arrhythmia, restoration of cardiac function, congestive heart failure, diabetes, asthma, respiratory disorders, ischemia-induced injury of the brain, heart and kidney, and diarrhea.

One preferred class of $A_1$ antagonists includes those compounds of Formula I in which $R^1$ is lower alkyl of 1–3 carbon atoms, particularly ethyl or n-propyl, Z is phenyl substituted with at least one member of the group consisting of halogen, optionally substituted $C_{1-3}$ alkyl, and $C_{1-3}$ alkoxy, and Y is $C_{1-3}$ alkylene, particularly methylene or ethylene. In another preferred class of compounds, $R^1$ is lower alkyl of 1–3 carbon atoms, particularly ethyl or n-propyl, Y is $C_{1-3}$ alkylene, particularly methylene or ethylene, and Z is unsubstituted phenyl.

Preferred $A_1$ antagonists include, but are not limited to:
$N^2$(2-phenylethyl)-9-propyl-8-(pyrazol-1-yl)-9H-purine-2,6-diamine;
$N^2$[2-(4-chlorophenyl)ethyl)-9-propyl-8-(pyrazol-1-yl)-9H-purine-2,6-diamine;
$N^2$[2-(2-chlorophenyl)ethyl)-9-propyl-8-(pyrazol-1-yl)-9H-purine-2,6-diamine;
$N^2$[2-(2,5-dimethoxyphenyl)ethyl)-9-propyl-8-(pyrazol-1-yl)-9H-purine-2,6-diamine;
$N^2$[2-(4-fluorophenyl)ethyl)-9-propyl-8-(pyrazol-1-yl)-9H-purine-2,6-diamine;

$N^2$[2-(3-fluorophenyl)ethyl)-9-propyl-8-(pyrazol-1-yl)-9H-purine-2,6-diamine;
$N^2$(3-aminomethylbenzyl)-9-propyl-8-(pyrazol-1-yl)-9H-purine-2,6-diamine;
$N^2$(4-aminomethylbenzyl)-9-propyl-8-(pyrazol-1-yl)-9H-purine-2,6-diamine;
$N^2$benzyl-8-(pyrazol-1-yl)-9H-purine-2,6-diamine;
$N^2$-benzyl-8-(3,5-dimethylpyrazol-1-yl)-9-ethyl-9H-purine-2,6-diamine;
($N^2$benzyl-8-[4-(4-methylphenyl)pyrazol-1-yl]-9-ethyl-9H-purine-2,6-diamine;
$N^2$benzyl-8-[4-(3-trifluoromethylphenyl)pyrazol-1-yl]-9-ethyl-9H-purine-2,6-diamine;
$N^2$benzyl-8-[4-(4-methoxyphenyl)pyrazol-1-yl]-9-ethyl-9H-purine-2,6-diamine;
$N^2$benzyl-8-[4-(4-fluorophenyl)pyrazol-1-yl]-9-ethyl-9H-purine-2,6-diamine; and
$N^2$benzyl-9-ethyl-8-(4-methylpyrazol-1-yl)-9H-purine-2,6-diamine.

Particularly preferred compounds include, but are not limited to:
$N^2$-(2-phenylethyl)-9-propyl-8-(pyrazol-1-yl)-9H-purine-2,6-diamine;
$N^2$-[2-(4-fluorophenyl)ethyl)-9-propyl-8-(pyrazol-1-yl)-9H-purine-2,6-diamine;
$N^2$-[2-(3-fluorophenyl)ethyl)-9-propyl-8-(pyrazol-1-yl)-9H-purine-2,6-diamine;
$N^2$-(4-fluorobenzyl)-9-ethyl-8-(1H-pyrazol-1-yl)-9H-purine-2,6-diamine;
$N^2$-(4-fluorophenethyl)-9-ethyl-8-(1H-pyrazol-1-yl)-9H-purine-2,6-diamine;
$N^2$-(4-fluorophenethyl)-9-methyl-8-(1H-pyrazol-1-yl)-9H-purine-2,6-diamine;
$N^2$-(4-fluorobenzyl)-9-methyl-8-(1H-pyrazol-1-yl)-9H-purine-2,6-diamine; and
$N^2$benzyl-8-(pyrazol-1-yl)-9-ethyl-9H-purine-2,6-diamine.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 2) an alkyl group as defined above that is interrupted by 1–5 atoms or groups independently chosen from oxygen, sulfur and —$NR_a$—, where $R_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or 3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—$CH_2$—), ethylene (—$CH_2CH_2$—), the propylene isomers (e.g., —$CH_2CH_2CH_2$—and —$CH(CH_3)CH_2$—) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO^2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or (2) an alkylene group as defined above that is interrupted by 1–5 atoms or groups independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH($NH_2$)$CH_2$—), methylaminoethylene (—CH(NHMe)$CH_2$—), 2-carboxypropylene isomers(—$CH_2$CH ($CO_2H$)$CH_2$—), ethoxyethyl (—$CH_2CH_2O$—$CH_2CH_2$—), ethylmethylaminoethyl (—$CH_2CH_2N(CH_3)CH_2CH_2$—), 1-ethoxy-2-(2-ethoxy-ethoxy)ethane (—$CH_2CH_2O$—$CH_2CH_2$—$OCH_2CH_2$—$OCH_2CH_2$—), and the like.

The term "aralkyl: refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is; optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=$CH_2$), 1-propylene or allyl (—$CH_2$CH=$CH_2$), isopropylene (—C($CH_3$)=$CH_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —$CH_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2;

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl may be optionally substituted as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, or optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, $CF_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is hydrogen, $R^2$ is ethyl, Y is methylene, and Z is phenyl:

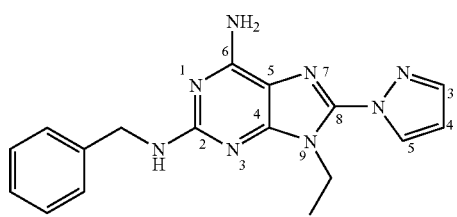

Formula I which is named:
N²-benzyl-8-(pyrazol-1-yl)-9-ethyl-9H-purine-2,6-diamine, also known as N2-benzyl-9-ethyl-8-(1H-pyrazol-1-yl)-9H-purine-2,6-diamine or [6-amino-8-(pyrazolyl)-9-ethylpurin-2-yl]benzylamine.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I may be prepared starting from 2,6-dichloropurine, as shown in Reaction Scheme I.

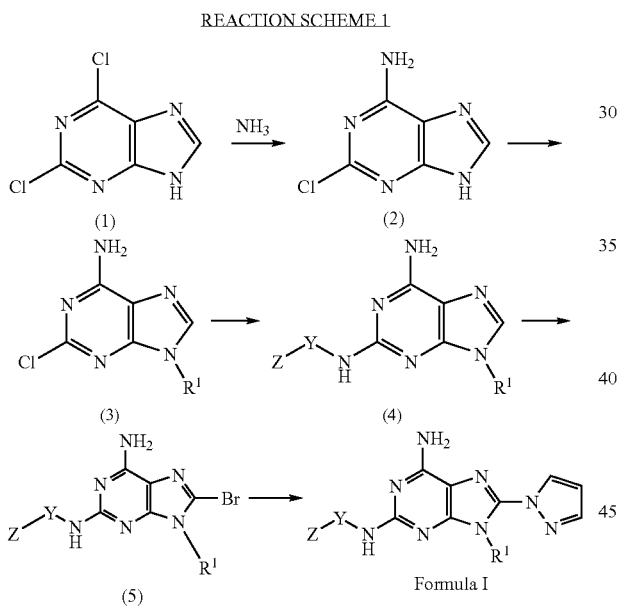

Step 1—Preparation of Formula (2)

The compound of formula (2) is prepared conventionally from the commercially available compound of formula (1), 2,6-dichloropurine, by reaction with ammonia under pressure in a protic solvent, for example methanol, at a temperature of 60–100° C., for about two days. When the reaction is substantially complete, the product of formula (2) is isolated by conventional means, for example removal of the solvent under reduced pressure.

Step 2—Preparation of Formula (3)

The compound of formula (2) is then converted to a compound of formula (3) by alkylation at the 9-position. The compound of formula (2) is reacted with a halide of formula R¹X, where R¹ is as defined above, with the proviso that it cannot be aryl, and X is chloro, bromo, or iodo, preferably iodo, in the presence of a base, preferably potassium carbonate, in a suitable solvent, preferably acetone. The reaction is preferably conducted at reflux, for about 18 hours. When the reaction is substantially complete, the product of formula (3) is isolated by conventional means, for example removal of the solvent under reduced pressure and slurrying with water before filtering.

Step 3—Preparation of Formula (4)

The 2-chloro moiety is then displaced from the compound of formula (3) by reaction with a compound of formula ZYNH₂ in the presence of a base. The reaction is carried out in an inert protic solvent, preferably n-butanol, at a temperature of about reflux, for about 24–48 hours. When the reaction is substantially complete, the product of formula (4) is isolated by conventional means, for example by removal of the solvent under reduced pressure, followed by chromatography of the residue on silica gel.

Step 4—Preparation of Formula (5)

The compound of formula (4) is then converted to the 8-bromo derivative of formula (5) by reaction with a suitable brominating agent, for example N-bromosuccinimide. The reaction is carried out in an inert solvent, preferably an ether, more preferably tetrahydrofuran, at about room temperature, for about 1–10 hours, preferably about 2 hours. When the reaction is substantially complete, the product of formula (5) is isolated by conventional means, for example by removal of the solvent under reduced pressure, followed by chromatography of the residue on silica gel.

Step 5—Preparation of Formula I

The compound of formula (5) is then converted to a compound of Formula I by reaction with an optionally substituted pyrazole in the presence of an alkali hydride, preferably sodium hydride. The reaction is carried out in an inert polar solvent, preferably dimethylformamide, at about 80° C., for about 18 hours. When the reaction is substantially complete, the product of Formula I is isolated by conventional means, for example by removal of the solvent under reduced pressure, partitioning between dichloromethane and water, separation of the organic layer, removal of solvent, followed by chromatography of the residue on silica gel.

An alternative method of introducing the pyrazole group to the 8-position of the purine is shown in Reaction Scheme 2.

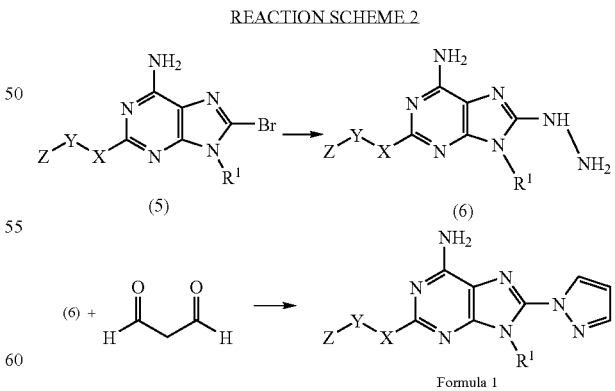

Step 1—Preparation of Formula (6)

The compound of formula (5) is converted to a compound of formula (6) by reaction with hydrazine hydrate. The reaction is carried out in a protic solvent, preferably ethanol, at about reflux, preferably about 80° C., for about 24 hours. When the reaction is substantially complete, the product of formula (6) is isolated by conventional means, for example by partitioning between ether and water, separation of the organic layer, drying the solvent, and removal of solvent under reduced pressure. The compound of Formula (6) is used for the next step without purification.

Step 2—Preparation of Formula I

The compound of formula (6) is converted to a compound of Formula I by reaction with malonaldehyde. The reaction is carried out in a protic solvent, preferably methanol/acetic mixture, at about reflux, for about 24 hours. When the reaction is substantially complete, the product of Formula I is isolated by conventional means, for example by removal of solvent under reduced pressure, followed by chromatography of the residue on silica gel, preferably TLC.

Preferred Processes and Last Steps

The compounds of the present invention can be prepared according to the following last steps:

Step 1. Contacting a compound of the formula

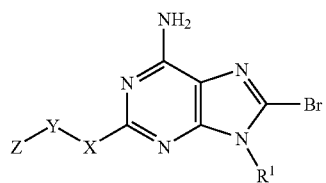

(5)

with an anion formed from a pyrazole of the formula:

and a strong base, preferably sodium hydride.

Step 2. Contacting a compound of formula (6):

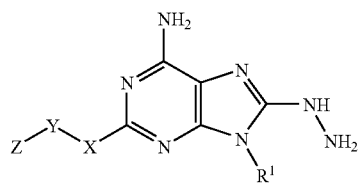

(6)

with malonaldehyde:

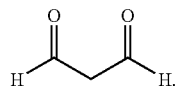

Utility, Testing and Administration

General Utility

The compounds of Formula I are effective in the treatment of conditions that respond to administration of $A_1$ adenosine receptor antagonists. Such conditions include, but are not limited to, disease states for which diuretic treatment is appropriate, renal failure, renal dysfunction, nephritis, hypertension, edema, Alzheimers disease, stress, depression, cardiac arrhythmia, restoration of cardiac function, congestive heart failure, diabetes, asthma, respiratory disorders, ischemia-induced injury of the brain, heart and kidney, and diarrhea.

The compounds of Formula I are also effective in the treatment of conditions that respond to administration of $A_2B$ adenosine receptor antagonists. Such conditions include, but are not limited to, diarrhea, atherosclerosis, restenosis, diabetic retinopathy, Type II diabetes, cancer, senile dementia, Alzheimer's disease, Parkinson's disease, traumatic brain injury, and Type I hypersensitivity reactions, including asthma, atopic eczema, and hay fever.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modem Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous, or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)-2-Chloropurine-6-ylamine

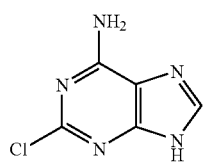

2

Ammonia was bubbled through 200 mL of methanol for 15 minutes, and the solution was added to 2,6-dichloropurine (10 g, 0.053 moles) in a steel bomb. The resulting mixture was then heated to 90° C. for 48 hours. Evaporation of the solvent followed by drying under vacuum afforded the compound of formula (2) (2-chloropurine-6-ylamine), as a yellow solid.

EXAMPLE 2

Preparation of a Compound of Formula (3)

A. Preparation of a Compound of Formula (3) where $R^1$ is Ethyl

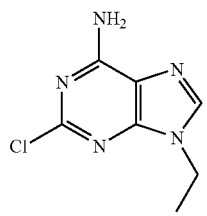

3

The compound of formula (2) (8.9 g, 0.053 mole), potassium carbonate (18.31 g, 0.133 mole), and ethyl iodide (6.36 mL, 0.08 moles) were combined in 100 mL of acetone and stirred at reflux for 18 hours. The mixture was cooled and the solvent evaporated. To the residue was added water (250 mL), and the mixture was filtered to give a compound of formula (3) where $R^1$ is ethyl (2-chloro-9-ethylpurine-6-ylamine), as a buff colored solid.

B. Preparation of a Compound of Formula (3) where $R^1$ is n-Propyl

Similarly, following the procedure of 1A above, but replacing ethyl iodide by n-propyl iodide, 2-chloro-9-(n-propyl)purine-6-ylamine was prepared.

C. Preparation of a Compound of Formula (3), varying $R^1$

Similarly, following the procedure of 1A above, but replacing ethyl iodide by compounds with suitable leaving groups, the following compounds of formula (3) are prepared:

2-chloro-9-methylpurine-6-ylamine;
2-chloro-9-(iso-propyl)purine-6-ylamine; and
2-chloro-9-(isobutyl)purine-6-ylamine;

D. Preparation of a Compound of Formula (3), varying $R^1$

Similarly, following the procedure of 1A above, but replacing ethyl iodide by compounds with suitable leaving groups, any compound of formula (3) may be prepared.

EXAMPLE 3

Preparation of a Compound of Formula (4)

A. Preparation of a Compound of Formula (4) where $R^1$ is Ethyl, Y is Methylene, and Z is Phenyl

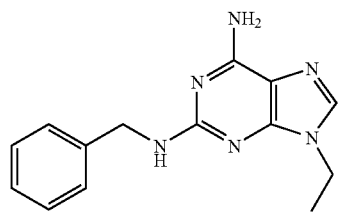

4

A compound of formula (3) where $R^1$ is ethyl (2-chloro-9-ethylpurine-6-ylamine) (0.9 g, 4.55 mmoles), triethylamine (1.27 mL, 9 mmoles), and benzylamine (1 mL, 9 mmoles) were mixed in 1-butanol (10 mL) and stirred at reflux for 24 hours. Another 1 mL of benzylamine was added and the refluxing continued for another 24 hours. Solvent was evaporated and the residue was residue was purified over a silica gel column (eluting with 5% methanol/dichloromethane) to give a compound of formula (4) where $R^1$ is ethyl, Y is methylene, and Z is phenyl ($N^2$ benzyl-9-ethyl-9H-purine-2,6-diamine), as a pale yellow solid.

B. Preparation of a Compound of Formula (4) where $R^1$ is Ethyl, Y is Ethylene, and Z is Phenyl Similarly, following the procedure of 3A above, but replacing benzylamine with 2-phenyethylamine, ($N^2$(2-phenylethyl)-9-ethyl-9H-purine-2,6-diamine) was prepared., a compound of formula (4).

C. Preparation of a Compound of Formula (4), varying Z, Y, and $R^1$

Similarly, following the procedure of 3A above, but optionally replacing 2-chloro-9-ethylpurine-6-ylamine) with other compounds of formula (3), and optionally replacing benzylamine with other amines of formula $ZYNH_2$, the following compounds of formula (4) are prepared.

$N^2$-benzyl-9-methylpurine-2,6-diamine;
$N^2$-benzyl-9-(iso-propyl)purine-6-diamine;
$N^2$benzyl-9-isobutyl-9H-purine-2,6-diamine), $N^2$(2-phenylethyl)-9-isopropyl-9H-purine-2,6-diamine), and $N^2$ (4-fluorobenzyl)-9-isopropyl-9H-purine-2,6-diamine).

EXAMPLE 4

Preparation of a Compound of Formula I

A. Preparation of a Compound of Formula I where $R^1$ is Ethyl, Y is Methylene, and Z is Phenyl

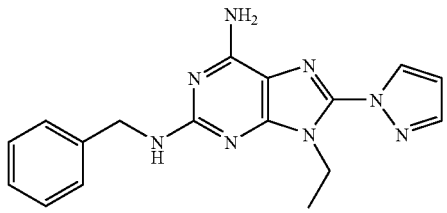

The compound of formula (4) where $R^1$ is ethyl, Y is methylene, and Z is phenyl (1 g, 3.72 mmoles) was dissolved in tetrahydrofuran (37.5 mL) and N-bromosuccinimide (0.73 g, 4.1 mmoles) added, and the mixture stirred at room temperature for 2 hours. The solvent was evaporated under reduced pressure, and the residue was purified on a silica gel column, eluting with 1:1 EtOAc:Hexanes to 2% methanol/dichloromethane, to give a compound of formula (5), $N^2$benzyl-8-bromo-9-ethyl-9H-purine-2,6-diamine, as an off-white solid.

This compound (0.5 g, 1.68 mmoles) was dissolved in DMF (5 mL) and added to a previously formed mixture of pyrazole (0.34 g, 5 mmoles) and 60% w/w NaH dispersion in DMF (10 mL). The reaction mixture was allowed to stir at 80° C. for 18 hours. The solvent was evaporated under reduced pressure, and the crude material was dissolved in 50 mL dichloromethane and washed with water (2×20 mL). The dichloromethane was dried (MgSO$_4$) and removed under reduced pressure, to give a residue that was purified by column chromatography (eluting with 30% EtOAc/hexanes to 75% EtOAc/hexanes) to give $N^2$ benzyl-8-(pyrazol-1-yl)-9-ethyl-9H-purine-2,6-diamine, as a pale yellow solid, which is a compound of Formula I where $R^1$ is ethyl, Y is methylene, and Z is phenyl B. Preparation of a Compound of Formula I where $R^1$ is Ethyl, Y is Ethylene, and Z is Phenyl Similarly, following the procedure of 4A above, but replacing the compound of formula (4) where $R^1$ is ethyl, Y is methylene, and Z is phenyl with a compound of formula (4) where $R^1$ is ethyl, Y is ethylene, and Z is phenyl, the compound of Formula I where $R^1$ is ethyl, Y is ethylene, and Z is phenyl, ($N^2$(2-phenylethyl)-8-(pyrazol-1-yl)-9-ethyl-9H-purine-2,6-diamine) was prepared.

Similarly, the following compounds of Formula I were prepared:

$N^2$(2-phenylethyl)-9-ethyl-8-(pyrazol-1-yl)-9H-purine-2,6-diamine;

$N^2$(2-phenylethyl)-9-propyl-8-(pyrazol-1-yl)-9H-purine-2,6-diamine;

$N^2$(3-phenylpropyl)-9-propyl-8-(pyrazol-1-yl)-9H-purine-2,6-diamine;

$N^2$[2-(2-fluorophenyl)ethyl)-9-propyl-8-(pyrazol-1-yl)-9H-purine-2,6-diamine.

$N^2$(2-phenylpropyl)-9-propyl-8-(pyrazol-1-yl)-9H-purine-2,6-diamine, R and S isomers;

$N^2$[2-(4-chlorophenyl)ethyl]-9-propyl-8-(pyrazol-1-yl)-9H-purine-2,6-diamine;

$N^2$[2-(2-chlorophenyl)ethyl]-9-propyl-8-(pyrazol-1-yl)-9H-purine-2,6-diamine;

$N^2$[2-(2,5-dimethoxyphenyl)ethyl]-9-propyl-8-(pyrazol-1-yl)-9H-purine-2,6-diamine;

$N^2$[2-(2,4-dichlorophenyl)ethyl]-9-propyl-8-(pyrazol-1-yl)-9H-purine-2,6-diamine;

$N^2$[2-(2-methoxyphenyl)ethyl]-9-propyl-8-(pyrazol-1-yl)-9H-purine-2,6-diamine;

$N^2$(2-hydroxymethyl)benzyl-9-propyl-8-(pyrazol-1-yl)-9H-purine-2,6-diamine;

$N^2$(4-aminomethylbenzyl)-9-propyl-8-(pyrazol-1-yl)-9H-purine-2,6-diamine;

$N^2$(3-aminomethylbenzyl)-9-propyl-8-(pyrazol-1-yl)-9H-purine-2,6-diamine;

$N^2$(2-aminomethylbenzyl)-9-propyl-8-(pyrazol-1-yl)-9H-purine-2,6-diamine;

$N^2$(4-hydroxymethyl)benzyl-9-propyl-8-(pyrazol-1-yl)-9H-purine-2,6-diamine;

$N^2$(3-hydroxymethyl)benzyl-9-propyl-8-(pyrazol-1-yl)-9H-purine-2,6-diamine;

$N^2$[2-(4-fluorophenyl)ethyl]-9-propyl-8-(pyrazol-1-yl)-9H-purine-2,6-diamine; and $N^2$[2-(3-fluorophenyl)ethyl]-9-propyl-8-(pyrazol-1-yl)-9H-purine-2,6-diamine;

C. Preparation of a Compound of Formula I, varying Z, Y, and $R^1$

Similarly, following the procedure of 4A above, but replacing the compound of formula (4) where $R^1$ is ethyl, $R^3$ is benzyl, and X is —NH— with other appropriately substituted compounds of formula (4), the following compounds of Formula I are prepared.

$N^2$benzyl-8-(pyrazol-1-yl)-9-methyl-9H-purine-2,6-diamine;

$N^2$benzyl-8-(pyrazol-1-yl)-9-isopropyl-9H-purine-2,6-diamine;

$N^2$benzyl-8-(pyrazol-1-yl)-9-isobutyl-9H-purine-2,6-diamine), $N^2$(2-phenylethyl)-8-(pyrazol-1-yl)-9-isopropyl-9H-purine-2,6-diamine), and $N^2$(4-fluorobenzyl)-8-(pyrazol-1-yl)-9-isopropyl-9H-purine-2,6-diamine).

EXAMPLE 5

Alternative Preparation of a Compound of Formula I

A. Preparation of a Compound of Formula (6) where $R^1$ is Ethyl, Y is Methylene, and Z is Phenyl

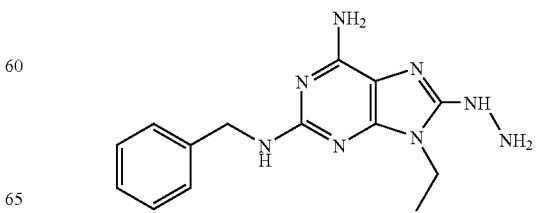

The compound of formula (5) where $R^1$ is ethyl, Y is methylene, and Z is phenyl (1.0 g, 2.9 mmoles) and hydrazine monohydrate (0.5 mL, 10.3 mmoles) were dissolved in ethanol (5 mL) and the mixture warmed to reflux for 24 hours. The precipitate obtained was stirred in ether for 30 minutes. The precipitate was filtered and dried to give a compound of formula (6) where $R^1$ is ethyl, Y is methylene, and Z is phenyl, which was used in the next step without further purification.

B. Preparation of a Compound of Formula I where $R^1$ is Hydrogen, $R^2$ is Ethyl, Y is Methylene, and Z is Phenyl

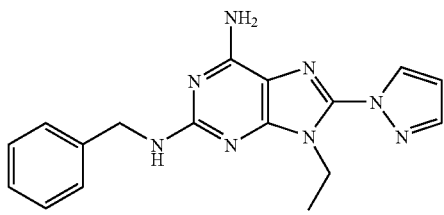

The crude compound of formula (6) where $R^1$ is hydrogen, $R^2$ is ethyl, Y is methylene, and Z is phenyl (0.1 g, 0.33 mmoles) is dissolved in 1:1 MeOH:AcOH solution (4 mL). To this solution is added malonaldehyde (0.5 mmoles), and the mixture is refluxed for 24 hours. The solvents are evaporated under reduced pressure, and the residue purified by preparative TLC (eluting with EtOAc) to give a compound of Formula I where $R^1$ is hydrogen, $R^2$ is ethyl, Y is methylene, and Z is phenyl.

C. Preparation of a Compound of Formula I, varying Z, Y, and $R^1$

Similarly, following the procedure of 5A above, but optionally replacing the compound of formula (5) where $R^1$ is ethyl, Y is methylene, and Z is phenyl with other compounds of formula (5) in 5A above, other compounds of Formula I are prepared.

EXAMPLE 6

Several compounds of Formula I prepared as shown in the above procedures were characterized by NMR and mass spectrometry. For example:

(6-amino-9-ethyl-8-pyrazolylpurin-2-yl)benzylamine
$^1$H NMR (400 MHz, DMSO-$d_6$): 8.20 (s, 1H), 7.83 (s, 1H), 7.40–7.05 (m, 5H), 6.90 (t, 1H), 6.75 (s, 2H), 6.53 (s, 1H), 4.41 (s, 2H), 4.08 (q, J=8 Hz, 2H), 1.12 (t, J=8 Hz, 3H).

(6-amino-9-propyl-8-pyrazolylpurin-2-yl)[2-(4-fluorophenyl)ethyl]amine
$^1$H NMR (400 MHz, DMSO-$d_6$): 8.31 (s, 1H), 7.92 (s, 1H), 7.35–7.29 (m, 2H), 7.16–7.10 (m, 2H), 6.84 (brs, 2H), 6.62 (s, 1H), 6.50 (brs, 1H), 4.16 (t, J=8 Hz, 2H), 3.46 (t, J=8 Hz, 2H), 2.86 (t, J=8 Hz, 2H), 1.70–1.60 9m, 2H), 0.79 (t, J=8 Hz, 3H).

(6-amino-9-propyl-8-pyrazolylpurin-2-yl)[2-(4-chlorophenyl)ethyl]amine
$^1$H NMR (400 MHz, DMSO-$d_6$): 8.31 (s, 1H), 7.92 (s, 1H), 7.36 (d, J=8 Hz, 2H), 7.31 (d, J=8 Hz, 2H), 6.85 (brs, 2H), 6.62 (s, 1H), 6.50 (brs, 1H), 4.16 (t, J=8 Hz, 2H), 3.46 (t, J=8 Hz, 2 H), 2.86 (t, J=8 Hz, 2H), 1.65 (q, J=8 Hz, 2H), 0.77 (t, J=8 Hz, 3H)

The following examples illustrate the preparation of representative pharmaceutical formulations containing a compound of Formula I, such as those prepared in accordance with Example 1.

EXAMPLE 7

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 8

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 9

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 10

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 11

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 12

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 13

A subcutaneous formulation may be prepared as follows:

| Ingredient | Quantity |
| --- | --- |
| Active Ingredient | 5.0 mg |
| Corn Oil | 1.0 mL |

EXAMPLE 14

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 15

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 16

Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably, the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 17

Adenosine Receptor Binding Assays

Stable Transfection of HEK-293 or CHO Cells

The cDNAs for human $A_1$, $A_{2A}$, $A_{2B}$ or $A_3$ AdoRs were prepared by RT-PCR from total RNA of human cells or tissues and sequenced on both strands. The expression vector containing each of these cDNAs and a second vector containing a neomycin or puromycin-resistance gene were introduced to HEK-293 or CHO cells by Lipofectin-Plus (Life Technology). Colonies were selected by growing transfected cells in the presence of neomycin or puromycin. Stably transfected cells were maintained in Dulbecco's modified Eagle's medium (DMEM) or F-12 medium with 10% fetal bovine serum, 100 µg/ml penicillin, 100 µg/ml streptomycin and appropriate concentrations of neomycin or puromycin. These stably transfected cells were referred to as HEK-"AdoR" or CHO-"AdoR" depending on the receptors that they express. The cell lines used routinely were CHO-$A_1$, HEK-$A_{2A}$, HEK-$A_{2B}$,and CHO-$A_3$ cells. In addition, hamster DDT1 MF-2 cells that express endogenous $A_1$ AdoRs were also used to determine the binding activities of compounds for $A_1$ AdoRs.

Membrane Preparation

Monolayers of transfected cells or DDT1 MF-2 were washed with phosphate buffered saline (PBS) and harvested in a buffer containing 10 mM HEPES (pH 7.4), 10 mM EDTA and protease inhibitors. The cells were homogenized in polytron for 1 minute at setting 4 and centrifuged at 29000 g for 15 minutes at 4° C. The cell pellets were washed with a buffer containing 10 mM HEPES (pH7.4), 1 mM EDTA and protease inhibitors, and were resuspended in the same buffer supplemented with 10% sucrose. Frozen aliquots were kept at −80° C.

Radioligand Binding

The affinities of compounds for $A_1$, $A_{2A}$, $A_{2B}$ or $A_3$ AdoRs were determined in competition studies using radioligands such as $^3$H-CPX ($A_1$ antagonist), or $^3$H-CCPA ($A_1$ agonist), $^3$H-ZM241385 ($A_{2A}$ antagonist) or $^3$H-CGS21680 ($A_{2A}$ agonist), $^3$H-ZM241385 ($A_{2B}$ antagonist) or $^{125}$I-AB-MECA ($A_3$ agonist) and membranes of corresponding cells. For example, to determine the affinity for $A_1$ AdoRs, the competition assays were started by mixing 0.5–1 nM $^3$H-CPX with various concentrations of test compounds and 25–100 µg membrane proteins of CHO-$A_1$ or DDT1 MF-2 in TE buffer (50 mM Tris and 1 mM EDTA) supplemented with 1 U/ml adenosine deaminase. The assays were incubated for 60–90 minutes, stopped by filtration onto GF/B filter plates using Packard Harvester and washed four times with ice-cold TM buffer (10 mM Tris, 1 mM MgCl2, pH 7.4). The amounts of radioligands that bound to the GF/B filter plates were determined by scintillation counting. Nonspecific binding was determined in the presence of 1–10 µM of cold ligands. $B_{max}$ and $K_D$ values were calculated using Graph-Pad software.

cAMP Measurements

Cells were harvested using 0.0025% trypsin and 2 mM EDTA in PBS, washed and resuspended in phenol-free DMEM to a concentration of $1 \times 10^6$ cells/ml, and then incubated with 1 U/ml of adenosine deaminase for 30 minutes at room temperature. Cells were then treated with various agonists, antagonists and/or forskolin in the presence or absence of 50 µM phosphodiesterase IV inhibitor, rolipram. After incubating for 5–30 minutes at 37° C., cells were lysed and cAMP concentrations were determined using cAMP-Screen Direct™ System (Applied Biosystem) according to the manufacturer's instructions.

The compounds of Formula I were demonstrated to be $A_{2B}$ and $A_1$ adenosine receptor agonists in the above-described assay. Representative examples of test data is presented in Table 1 below.

TABLE 1

| Compound | Ki ($A_{2B}$) nM | Ki ($A_1$) nM |
| --- | --- | --- |
| (6-amino-9-propyl-8-pyrazolylpurin-2-yl)(2-phenylethyl)amine | 500 | 113 |
| (6-amino-9-propyl-8-pyrazolylpurin-2-yl)[2-(4-chlorophenyl)ethyl]amine | 5000 | 1090 |
| (6-amino-9-propyl-8-pyrazolylpurin-2-yl)[2-(2-chlorophenyl)ethyl]amine | 3643 | 382 |
| (6-amino-9-propyl-8-pyrazolylpurin-2-yl)[2-(2,5-dimethoxyphenyl)ethyl]amine | 1681 | 182 |
| (6-amino-9-propyl-8-pyrazolylpurin-2-yl)[2-(4-fluorophenyl)ethyl]amine | 2300 | 66 |
| (6-amino-9-propyl-8-pyrazolylpurin-2-yl)[2-(3-fluorophenyl)ethyl]amine | 160 | 28 |
| {[3-(aminomethyl)phenyl]methyl}(6-amino-9-propyl-8-pyrazolylpurin-2-yl)amine | 7000 | 408 |
| (4-{[(6-amino-9-propyl-8-pyrazolylpurin-2-yl)amino]methyl}phenyl)methan-1-ol | 7000 | 1789 |
| (6-amino-9-ethyl-8-pyrazolylpurin-2-yl)benzylamine | 1000 | 15 |

The invention claimed is:

1. A method of antagonizing $A_1$ adenosine receptors in a mammal in order to treat a disease state chosen from renal failure, renal dysfunction, nephritis, hypertension, edema, stress, depression, cardiac arrhythmia, impairment of cardiac function, congestive heart failure, and ischemia-induced injury of the brain, heart and kidney, comprising administering to a mammal a therapeutically effective dose of a compound having the structure of Formula I

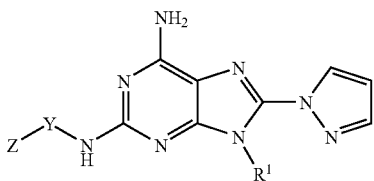

Formula I wherein:
- $R^1$ is optionally substituted $C_{1-14}$ alkyl;
- Y is $C_{1-14}$ alkylene; and
- Z is phenyl that is optionally substituted with halo, hydroxy, amino, cyano, or optionally substituted $C_{1-4}$ alkyl, or a pharmaceutically acceptable salt, ester, or prodrug thereof.

2. The method of claim 1, wherein $R^1$ is methyl, ethyl, or propyl and Y is methylene or ethylene.

3. The method of claim 2, wherein Z is phenyl optionally substituted by 1–3 substituents independently chosen from chloro, fluoro, methoxy, and hydroxy.

4. The method of claim 3, wherein Z is 3-fluorophenyl, $R^1$ is n-propyl, and Y is ethylene, and the compound of formula I is $N^2$ [2-(3-fluorophenyl)ethyl]-9-propyl-8-(pyrazol-1-yl)-9H-purine-2,6-diamine.

5. The method of claim 3, wherein Z is phenyl, $R^1$ is ethyl, and Y is methylene, and the compound of formula I is $N^2$-benzyl-8-pyrazol-1-yl-9-ethyl-9H-purine-2,6-diamine.

6. The method of claim 3, wherein Z is 4-fluorophenyl, $R^1$ is ethyl, and Y is methylene, and the compound of formula I is $N^2$-(4-fluorobenzyl)-9-ethyl-8-(1H-pyrazol-1-yl)-9H-purine-2,6-diamine.

7. The method of claim 3, wherein Z is 4-fluorophenyl, $R^1$ is ethyl, and Y is ethylene, and the compound of formula I is $N^2$-(4-fluorophenylethyl)-9-ethyl-8-(1H-pyrazol-1-yl)-9H-purine-2,6-diamine.

8. The method of claim 3, wherein Z is 4-fluorophenyl, $R^1$ is methyl, and Y is methylene, and the compound of formula I is $N^2$-(4-fluorobenzyl)-9-methyl-8-(1H-pyrazol-1-yl)-9H-purine-2,6-diamine.

9. The method of claim 3, wherein Z is 4-fluorophenyl, $R^1$ is methyl, and Y is ethylene, and the compound of formula I is $N^2$-(4-fluorophenylethyl)-9-methyl-8-(1H-pyrazol-1-yl)-9H-purine-2,6-diamine.

* * * * *